(12) United States Patent
Solar

(10) Patent No.: US 8,116,850 B2
(45) Date of Patent: Feb. 14, 2012

(54) ORGAN ACCESS DEVICE AND METHOD

(75) Inventor: Matthew S. Solar, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 53 days.

(21) Appl. No.: 12/615,182

(22) Filed: Nov. 9, 2009

(65) Prior Publication Data
US 2010/0057008 A1 Mar. 4, 2010

Related U.S. Application Data

(63) Continuation of application No. 10/325,615, filed on Dec. 20, 2002, now Pat. No. 7,636,596.

(51) Int. Cl.
A61B 5/05 (2006.01)
(52) U.S. Cl. ...................... 600/429; 606/130
(58) Field of Classification Search .......... 606/129, 606/130, 96, 98; 604/164.01; 600/201, 401, 600/429, 426
See application file for complete search history.

(56) References Cited

U.S. PATENT DOCUMENTS

| 431,187 A | 7/1890 | Foster |
|---|---|---|
| 438,801 A | 10/1890 | Delehanty |
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |
| 2,686,890 A | 8/1954 | Davis |
| 3,010,347 A | 11/1961 | Kron |
| 3,016,899 A | 1/1962 | Stenvall |
| 3,017,887 A | 1/1962 | Heyer |
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |
| 3,402,710 A | 9/1968 | Paleschuck |

(Continued)

FOREIGN PATENT DOCUMENTS

DE 3108766 9/1982

(Continued)

OTHER PUBLICATIONS

"Cross-Hairs Kit", Elekta Instruction for Use Brochure, pp. 2-5.

(Continued)

Primary Examiner — Victor Nguyen
(74) Attorney, Agent, or Firm — Scott A. Marks; Harness Dickey & Pierce, PLC

(57) ABSTRACT

An insertion guide device guides an instrument toward a target location in a subject. The insertion guide device includes a base portion securable to the subject and an insertion guide portion defining an insertion axis. The insertion guide portion guides the instrument along the insertion axis, and the insertion guide portion is moveably supported by the base portion for movement of the insertion axis about at least two axes. Moreover, the insertion guide device includes a locking device that selectively fixes the insertion guide portion relative to the base portion. The locking device selectively fixes the insertion axis relative to the at least two axes substantially concurrently.

18 Claims, 10 Drawing Sheets

U.S. PATENT DOCUMENTS

| | | |
|---|---|---|
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew et al. |
| 3,817,249 A | 6/1974 | Nicholson |
| 3,893,449 A | 7/1975 | Lee et al. |
| 3,981,079 A | 9/1976 | Lenczycki |
| 4,013,080 A | 3/1977 | Froning |
| 4,026,276 A | 5/1977 | Chubbuck |
| 4,040,427 A | 8/1977 | Winnie |
| 4,131,257 A | 12/1978 | Sterling |
| 4,230,117 A | 10/1980 | Anichkov et al. |
| 4,265,252 A | 5/1981 | Chubbuck et al. |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen |
| 4,618,978 A | 10/1986 | Cosman |
| 4,629,451 A | 12/1986 | Winters et al. |
| 4,638,798 A | 1/1987 | Shelden et al. |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson et al. |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,798,208 A | 1/1989 | Faasse, Jr. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist et al. |
| 5,116,345 A | 5/1992 | Jewell et al. |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson |
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,242,415 A | 9/1993 | Kantrowitz et al. |
| 5,246,448 A | 9/1993 | Chang |
| 5,257,998 A | 11/1993 | Ota et al. |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab |
| 5,306,272 A | 4/1994 | Cohen et al. |
| 5,309,913 A | 5/1994 | Kormos et al. |
| 5,330,485 A | 7/1994 | Clayman et al. |
| 5,354,283 A | 10/1994 | Bark et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,394,457 A | 2/1995 | Leibinger et al. |
| 5,405,330 A | 4/1995 | Zunitch et al. |
| 5,423,832 A | 6/1995 | Gildenberg |
| 5,423,848 A | 6/1995 | Washizuka et al. |
| 5,445,166 A | 8/1995 | Taylor |
| 5,452,720 A | 9/1995 | Smith et al. |
| 5,464,446 A | 11/1995 | Dreessen et al. |
| 5,470,307 A | 11/1995 | Lindall |
| 5,474,564 A | 12/1995 | Clayman et al. |
| 5,483,961 A | 1/1996 | Kelly et al. |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. |
| 5,528,652 A | 6/1996 | Smith et al. |
| 5,541,377 A | 7/1996 | Stuhlmacher |
| 5,572,905 A | 11/1996 | Cook, Jr. |
| 5,572,999 A | 11/1996 | Funda et al. |
| 5,575,798 A | 11/1996 | Koutrouvelis |
| 5,618,288 A | 4/1997 | Calvo et al. |
| 5,622,170 A | 4/1997 | Schulz |
| 5,638,819 A | 6/1997 | Manwaring et al. |
| 5,639,276 A | 6/1997 | Weinstock et al. |
| 5,643,286 A | 7/1997 | Warner et al. |
| 5,647,361 A | 7/1997 | Damadian |
| 5,649,936 A | 7/1997 | Real |
| 5,658,272 A | 8/1997 | Hasson |
| 5,662,600 A | 9/1997 | Watson et al. |
| 5,667,514 A | 9/1997 | Heller |

| | | |
|---|---|---|
| 5,695,501 A | 12/1997 | Carol et al. |
| 5,713,858 A | 2/1998 | Heruth et al. |
| 5,755,697 A | 5/1998 | Jones et al. |
| 5,776,064 A | 7/1998 | Kalfas et al. |
| 5,776,143 A | 7/1998 | Adams et al. |
| 5,776,144 A | 7/1998 | Leysieffer et al. |
| 5,788,713 A | 8/1998 | Dubach et al. |
| 5,807,033 A | 9/1998 | Benway |
| 5,809,694 A | 9/1998 | Postans et al. |
| 5,810,712 A | 9/1998 | Dunn |
| 5,817,106 A | 10/1998 | Real |
| 5,823,975 A | 10/1998 | Stark et al. |
| 5,833,627 A | 11/1998 | Shmulewitz et al. |
| 5,843,150 A | 12/1998 | Dreessen et al. |
| 5,851,183 A | 12/1998 | Bucholz |
| 5,865,817 A | 2/1999 | Moenning et al. |
| 5,865,842 A | 2/1999 | Knuth et al. |
| 5,871,445 A | 2/1999 | Bucholz |
| 5,871,487 A | 2/1999 | Warner et al. |
| 5,873,822 A | 2/1999 | Ferre et al. |
| 5,891,034 A | 4/1999 | Bucholz |
| 5,891,157 A | 4/1999 | Day et al. |
| 5,927,277 A | 7/1999 | Baudino et al. |
| 5,950,629 A | 9/1999 | Taylor et al. |
| 5,954,687 A | 9/1999 | Baudino |
| 5,957,933 A | 9/1999 | Yanof et al. |
| 5,957,934 A | 9/1999 | Rapoport et al. |
| 5,964,705 A | 10/1999 | Truwit et al. |
| 5,980,535 A | 11/1999 | Barnett et al. |
| 5,984,930 A | 11/1999 | Maciunas et al. |
| 5,993,463 A * | 11/1999 | Truwit ............................. 606/130 |
| 5,997,471 A | 12/1999 | Gumb et al. |
| 6,006,126 A | 12/1999 | Cosman |
| 6,018,094 A | 1/2000 | Fox |
| 6,021,343 A | 2/2000 | Foley et al. |
| 6,024,729 A | 2/2000 | Dehdashtian et al. |
| 6,030,223 A | 2/2000 | Sugimori |
| 6,039,725 A | 3/2000 | Moenning et al. |
| 6,042,540 A | 3/2000 | Johnston et al. |
| 6,044,304 A | 3/2000 | Baudino |
| 6,058,323 A | 5/2000 | Lemelson |
| 6,071,288 A | 6/2000 | Carol et al. |
| 6,076,008 A | 6/2000 | Bucholz |
| 6,079,681 A | 6/2000 | Stern et al. |
| 6,110,182 A | 8/2000 | Mowlai-Ashtiani |
| 6,117,143 A | 9/2000 | Hynes et al. |
| 6,120,465 A | 9/2000 | Guthrie et al. |
| 6,135,946 A | 10/2000 | Konen et al. |
| 6,179,826 B1 | 1/2001 | Aebischer et al. |
| 6,195,577 B1 | 2/2001 | Truwit et al. |
| 6,206,890 B1 | 3/2001 | Truwit |
| 6,210,417 B1 | 4/2001 | Baudino et al. |
| 6,231,526 B1 | 5/2001 | Taylor et al. |
| 6,236,875 B1 | 5/2001 | Bucholz et al. |
| 6,238,402 B1 | 5/2001 | Sullivan, III et al. |
| 6,254,532 B1 | 7/2001 | Paolitto et al. |
| 6,257,407 B1 | 7/2001 | Truwit et al. |
| 6,261,300 B1 | 7/2001 | Carol et al. |
| 6,267,769 B1 | 7/2001 | Truwit |
| 6,267,770 B1 | 7/2001 | Truwit |
| 6,273,896 B1 | 8/2001 | Franck et al. |
| 6,282,437 B1 | 8/2001 | Franck et al. |
| 6,290,644 B1 | 9/2001 | Green, II et al. |
| 6,298,262 B1 | 10/2001 | Franck et al. |
| 6,315,770 B1 | 11/2001 | de la Torre et al. |
| 6,321,104 B1 | 11/2001 | Gielen et al. |
| 6,327,491 B1 | 12/2001 | Franklin et al. |
| 6,356,792 B1 | 3/2002 | Errico et al. |
| 6,368,329 B1 | 4/2002 | Truwit |
| 6,400,992 B1 | 6/2002 | Borgersen et al. |
| 6,457,963 B1 | 10/2002 | Tawara et al. |
| 6,482,182 B1 | 11/2002 | Carroll et al. |
| 6,488,620 B1 | 12/2002 | Segermark et al. |
| 6,491,699 B1 | 12/2002 | Henderson et al. |
| 6,529,765 B1 | 3/2003 | Franck et al. |
| 6,537,232 B1 | 3/2003 | Kucharczyk et al. |
| 6,546,277 B1 | 4/2003 | Franck et al. |
| 6,546,279 B1 | 4/2003 | Bova et al. |
| 6,547,795 B2 | 4/2003 | Schneiderman |
| 6,556,857 B1 | 4/2003 | Estes et al. |
| 6,609,020 B2 | 8/2003 | Gill |
| 6,610,100 B2 | 8/2003 | Phelps et al. |
| 6,632,184 B1 | 10/2003 | Truwit |
| 6,655,014 B1 | 12/2003 | Babini |
| 6,662,035 B2 | 12/2003 | Sochor |
| 6,676,669 B2 | 1/2004 | Charles et al. |
| 6,706,050 B1 | 3/2004 | Giannadakis |
| 6,726,678 B1 | 4/2004 | Nelson et al. |
| 6,746,471 B2 | 6/2004 | Mortier et al. |
| 6,752,812 B1 | 6/2004 | Truwit |
| 6,765,122 B1 | 7/2004 | Stout |
| 6,773,443 B2 | 8/2004 | Truwit et al. |
| 6,782,288 B2 | 8/2004 | Truwit et al. |
| 6,802,323 B1 | 10/2004 | Truwit et al. |
| 6,902,569 B2 | 6/2005 | Parmer et al. |
| 6,913,478 B2 | 7/2005 | Lamirey et al. |
| 6,944,895 B2 | 9/2005 | Truwit |
| 6,960,216 B2 | 11/2005 | Kolb et al. |
| 7,204,840 B2 * | 4/2007 | Skakoon et al. ............... 606/129 |
| 7,366,561 B2 | 4/2008 | Mills et al. |
| 7,479,146 B2 | 1/2009 | Malinowski |
| 2001/0014771 A1 | 8/2001 | Truwit et al. |
| 2001/0027271 A1 | 10/2001 | Franck et al. |
| 2001/0037524 A1 | 11/2001 | Truwit |
| 2002/0010479 A1 | 1/2002 | Skakoon et al. |
| 2002/0019641 A1 | 2/2002 | Truwit |
| 2002/0022847 A1 | 2/2002 | Ray et al. |
| 2002/0052610 A1 | 5/2002 | Skakoon et al. |
| 2002/0077646 A1 | 6/2002 | Truwit et al. |
| 2002/0156372 A1 | 10/2002 | Skakoon et al. |
| 2003/0079287 A1 | 5/2003 | Truwit |
| 2003/0187351 A1 | 10/2003 | Franck et al. |
| 2003/0208122 A1 | 11/2003 | Melkent et al. |
| 2004/0026161 A1 | 2/2004 | Takatsuka et al. |
| 2004/0059260 A1 | 3/2004 | Truwit |
| 2004/0176750 A1 | 9/2004 | Nelson et al. |
| 2004/0243147 A1 | 12/2004 | Lipow |
| 2004/0255991 A1 | 12/2004 | Truwit et al. |
| 2004/0260323 A1 | 12/2004 | Truwit et al. |
| 2004/0267284 A1 | 12/2004 | Parmer et al. |
| 2006/0122627 A1 | 6/2006 | Miller et al. |
| 2006/0192319 A1 | 8/2006 | Solar |
| 2006/0195119 A1 | 8/2006 | Mazzocchi et al. |
| 2007/0250078 A1 | 10/2007 | Stuart |
| 2007/0299427 A1 | 12/2007 | Yeung et al. |
| 2008/0004632 A1 | 1/2008 | Sutherland et al. |

FOREIGN PATENT DOCUMENTS

| | | |
|---|---|---|
| DE | 3937052 | 5/1990 |
| DE | 19726141 | 1/1999 |
| DE | 29612100 | 8/1999 |
| DE | 19808220 | 9/1999 |
| DE | 19820808 | 9/1999 |
| DE | 19826078 | 11/1999 |
| EP | 0386936 | 5/1990 |
| EP | 0427358 | 5/1991 |
| EP | 0724865 | 5/1991 |
| EP | 0609085 | 8/1994 |
| EP | 0832611 | 4/1998 |
| EP | 0904741 | 3/1999 |
| GB | 2237993 | 5/1991 |
| GB | 2329473 | 4/1998 |
| GB | 2346573 | 8/2000 |
| WO | WO-8809151 | 12/1988 |
| WO | WO-9721380 | 12/1988 |
| WO | WO-9522297 | 8/1995 |
| WO | WO-9610368 | 4/1996 |
| WO | WO-9633766 | 10/1996 |
| WO | WO-9703609 | 2/1997 |
| WO | WO-9742870 | 11/1997 |
| WO | WO-9817191 | 4/1998 |
| WO | WO-9825535 | 6/1998 |
| WO | WO-9851229 | 11/1998 |
| WO | WO-0001316 | 1/2000 |
| WO | WO-0018306 | 1/2000 |
| WO | WO-0124709 | 4/2001 |

| WO | WO-0149197 | 7/2001 |
| WO | WO-0176498 | 7/2001 |
| WO | WO-2004026161 A2 | 4/2004 |

OTHER PUBLICATIONS

"CRW™—Tyco Healthcare Radionics", Tyco Product Brochure, pp. 1-7.

"Fathom Remote Introducer", Image-Guided Neurologics, Inc., CNS Hynes Convention Center, 2p., (Oct. 30-Nov. 4, 1999).

"Inomed Competence in Neurophysiologic Monitoring", http://www.inomed.com/english/index.htm, (observed Mar. 23, 2004), 2 pgs.

"Leksell Stereotactic System", Elekta Product Brochure, pp. 1-6.

"MicroTargeting® Precision Guidance Using Microelectrode Recording", (Aug. 15, 2003), 5 pgs.

"Possible Existence of Common Internalization Mechanisms among Arginine-rich Peptides", Suzuki, T. et al., Journal of Biological Chemistry, vol. 277, No. 4 (2002) pp. 2437-2443.

Allison, S., et al "Microchannel Plate Intensifier Response in Traverse Magnetic Field", Electronic Letters, 26, (Jun. 7, 1990), 770-771.

Drake, J.M., et al. "ISG Viewing Wand System", Neurosurgery, 34 (6), (Jun. 1994), 1094-1097.

Dyer, P.V., et al., "The ISG Viewing Wand: an Application to Atlanto-Axial Cervical Surgery Using the Le for I Maxillary Osteotomy", British Journal of Oral and Maxillofacial Surgery, 33, (1995), 370-374.

Franck Joel, et al., "microTargeting® Platform System incorporating StarFix™ guidance", microTargeting, pp. 1-44.

Franck, Joel, et al., "microTargeting® Platform incorporating StarFix™ guidance", *microTargeting*, 3 pgs.

Gehring, W. J., "Homeodomain Proteins", Annu. Rev. Biochem., vol. 63 (1997) pp. 487-526.

Gillies, G., et al., "Magnetic Manipulation Instrumentation for Medical Physics Research", Review of Scientific Instruments, 65 (3), Review Article, (Mar. 1994), 533-562.

Grady, M., "Nonlinear Magnetic Stereotaxis:Three-Dimensional, in vivo Remote Magnetic Manipulation of a Small Object in Canine Brain", Medical Physics, 17 (3), (May/Jun. 1990), pp. 405-415.

Grady, M., et al., "Initial Experimental Results of a New Stereotaxic Hyperthermia System", American College of Surgeons: 1998 Clinical Congress: Surgical Forum, 39, (1998), 507-509.

Grady, M., et al., "Magnetic Stereotaxis System for Neurosurgical Procedures", Proc. 37th International Instrumentation Symp., Sand Diego, CA (May 1991), 665-675.

Grady, M., et al., "Magnetic Stereotaxis: A Technique to Deliver Stereotactic Hyperthermia", Neurosurgery, 27 (6), Technical Note, (Dec. 1990), pp. 1010-1016.

Grady, M., et al., "Preliminary Experimental Investigation of in vivo Magnetic Manipulation: Results and Potential Application in Hyperthermia", medical Physics, 16 (2), (Mar./Apr. 1989), pp. 263-272.

Hata, N., et al., "Needle Insertion Manipulator for CT- and MR-Guided Stereotactic Neurosurgery", Interventional MR:Techniques and Clinical Experience, St. Louis: London: Mosby; Martin Dunitz, F. Jolesz and I. Young, eds., (1998), 99-106.

Hirschberg, H., et al., "Image-Guided Neurosurgery—MR compatible stereotactic equipment", http:www.medinnova.no/English/P51466ster.html. (Mar. 29, 2001), 1p.

Hirschberg, Henry, et al., "Image-guided neurosurgery", stereotactic equipment for MR imaging, http://www.medinnova.no/English/P51466ster.html, (Observed Mar. 8, 2002), 1 page.

Howard, M., et al., "Magnetic Movement of a Brain Thermocepter", Neurosurgery, 24 (3), (1989), 444-448.

Howard, M., et al., "Magnetic Neurosurgery", Stereotactic and Functional Neurosurgery, 66, (1996), 102-107.

Howard, M., et al., "Magnetic Neurosurgery: Image-Guided, Remote-Controlled Movement of Neurosurgical Implants", Ch. 26 in: Clinical Neurosurgery: Proceedings of the Congress of Neurological Surgeons, San Francisco, CA, (1995), 382-391.

Howard, M., et al., "Review of Magnetic Neurosurgery Research", J. Image Guided Surgery, 1, (Nov. 1995), 295-299.

International Search Report and Written Opinion for PCT/US05/43651 mailed May 8, 2008.

Lawson, M., et al., "Near Real-Time Bi-planar Fluoroscopic Tracking System for the Video Tumor Fighter", SPIE, 1445, (1991), 265-275.

Leggett, W.B., et al. "Surgical Technology—The Viewing Wand: A New System for Three-Dimensional Computed Tomography-Correlated Intraoperative Localization", Current Surgery, (Dec. 1991), 674-678.

Malison, R.T., et al., "Computer-Assisted Coregistration of Multislice SPECT and MR Brain Images by Fixed External Fiducials", Journal of Computer Assisted Tomography, 17 (6), (1993), pp. 952-960.

Mannervik, M., "Target genes of homeodomain proteins", BioEssays vol. 21.4 (Apr. 1999) pp. 267-270.

McNeil., R., et al., "Characteristics of an Improved Magnetic-Implant Guidance System", IEEE Transactions on Biomedical Engineering, 42 (8), (Aug. 1995), 802-808.

McNeil., R., et al., "Functional Design Features and Initial Performance Characteristics of a Magnetic-Implant Guidance System for Stereotactic Neurosurgery", IEEE Transactions on Biomedical Engineering, 42 (8), (1995), 793-801.

Meeker, D., et al., "Optimal Realization of Arbitrary Forces in a Magnetic Stereotaxis System," IEEE Transactions on Magnetics, 32 (2), (Mar. 1996), 320-328.

Molloy, J., et al., "Experimental Determination of the Force Required for Insertion of a Thermoseed into Deep Brain Tissues", Annals of Biomedical Engineering, 18, (1990), 299-313.

Molly, J., et al., "Thermodynamics of Movable Inductively Heated Seeds for the Treatment of Brain Tumors", Medical Physics, 18 (4), (1991), 794-803.

Oliver, L, "Cup-And-Ball Chemopallidectomy Apparatus", (1958), p. 401.

Patikoglou, G. et al., "Eukaryotic Transcription Factor-DNA Complexes", Annual Review of Biophysics and Biomolecular Structure vol. 26 (1997) pp. 289-325.

Quate, E., et al., "Goniometric Motion Controller for the Superconducting Coil in a Magnetic Stereotaxis System", IEEE Transactions on Biomedical Engineering, 38 (9), (Sep. 1991), 899-905.

Ramos, P., et al., "Electro-Optic Imaging Chain for a Biplanar Fluoroscope for Neurosurgery: Magnetic Field Sensitivity and Contrast Measurements", Optical Engineering 32, (7), (1993), 1644-1656.

Ramos, P., et al., "Low-Dose, Magnetic Field-Immune, Bi-Planar Fluoroscopy for Neurosurgery", Proc. SPIE, 1443 (Medical Imaging V: Image Physics), (1991), 160-170.

Ramos, P., et al., "Microchannel Plate Image Intensifier Electron Dynamics in Magnetic Field", Electronics Letters, 27 (18), (Aug. 29, 1991), pp. 1636-1638.

Ritter, R., et al., "Magnetic Stereotaxis: Computer-Assisted, Image-Guided Remote Movement of Implants in the Brain", Ch. 26 in: Computer-Integrated Technology and Clinical Applications, MIT Press, Cambridge, MA., Taylor, R., et al., eds., (1996), 363-369.

Ritter, R., et al., "Magnetic Sterotaxis: An Application of Magnetic Control Technology to the Needs of Clinical Medicine", Proc. Of the MAG'95 Industrial Conf. and Exhibition, Technomic Pub. Co., Lancaster, PA., Allaire, P., ed., (1995), 186-193.

Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.

Sandeman, D.S., et al., "Advances in image-directed neurosurgery: Preliminary experience with the ISG Viewing Wand compared with the Leksell G frame", British Journal of Neurosurgery, 8 (199), pp. 529-544.

Stein, S. et al., "Checklist: Vertebrate homeobox genes", Mechanisms of Development, vol. 55, No. 1 (Mar. 1996) pp. 91-108.

Supplementary European Search Report mailed Oct. 26, 2009 for EP05852969 filed Dec. 6, 2005 claiming benefit of U.S. Appl. No. 11/005,907, filed Dec. 5, 2004.

Szikora, I., et al., "Endovascular Treatment of Experimental Aneurysms with Liquid Polymers: The Protective Potential of Stents", Neurosurgery, 38, (Feb. 1996), 339-347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

Yeh, H.S., et al., "Implantation of intracerebral depth electrodes for monitoring seizures using the Pelorus stereotactic system guided by magnetic resonance imaging", J. Neurosurg., 78 (1993), pp. 138-141.

Zinreich, S.J., et al., "Frameless Sterotaxic Integration of CT Imaging Data: Accuracy and Initial Applications", Radiology, 188 (3), (1993), pp. 735-742.

European Office Action mailed Jan. 22, 2010 for European Application No. 05 852 969.4.

* cited by examiner

ORGAN ACCESS DEVICE AND METHOD

CROSS-REFERENCE TO RELATED APPLICATIONS

This application is a continuation of U.S. patent application Ser. No. 10/325,615, filed on Dec. 20, 2002, issued as U.S. Pat. No. 7,636,596. The entire disclosure of the above application is incorporated herein by reference in its entirety.

FIELD

The present disclosure relates to an organ access device and method. Specifically, the invention relates to trajectory guidance of medical devices for procedures such as catheter or lead insertion.

BACKGROUND

This section provides background information related to the present disclosure which is not necessarily prior art.

A desire to reduce the disturbance of tissue during surgical procedures drives methods and devices for surgical insertion such as catheter insertion. The term "catheter" as used in this document is a broad term that generally describes an elongated tube for insertion into a region of a subject. Catheters include, but are not limited to, drug delivery catheters, optical catheters, micro-catheters, host catheters, etc. A small diameter catheter can be inserted into a subject along an insertion trajectory towards a target location within the subject with a minimal disturbance to surrounding tissue.

A drawback to catheter insertion procedures is that the target location is hidden within the subject. Only a small opening in the subject allows insertion of the catheter. Imaging techniques such as computed tomography (CT), magnetic resonance imaging (MRI) ultrasonic imaging, etc. are helpful in guiding a surgeon or other operator to insert the catheter towards the target location within the subject. Insertion guide devices are also useful in guiding the surgeon.

Local mounted insertion guide devices are desirable, in contrast to other guide devices such as head frames as used in neurosurgery. Local mounted insertion guide devices are not as cumbersome as head frames due to their light weight and smaller size. The subject does not need to be immobilized after imaging as is the case with head frame technology. Local mounted insertion guide devices are also less expensive to manufacture. In many instances they are fabricated from plastic materials, and may be disposable. Further, in contrast to head frame technology, local mounted insertion guide devices allow a subject to break up a surgical procedure into at least two different visits to the hospital.

One visit may include imaging, where a number of reference points called fiducial markers are attached to a subject. A target location tissue is imaged along with the fiducial markers, thus giving the surgeon a reference location of the target location in relation to the fiducial markers. If the fiducial markers are left secured to the subject, the subject may now return home and complete a surgical procedure at a second visit because the fiducial markers preserve a reference frame for the surgeon to target and work with. This was not possible using head frame technology, where a subject needed to remain secured inside a head frame until after completion of the surgical procedure.

Using a local mounting technique, an insertion guide device is also attached to the subject. The function of the insertion guide device is to guide a catheter along an axis into the subject to the target location where a selected operation such as drug delivery, tissue removal, etc. is performed.

A difficulty with this procedure arises in location tolerance when the insertion guide device is attached to the subject. In neurosurgery, the insertion guide device is frequently attached to the subject's skull using bone screws. The screws may not center in their ideal location, making precise alignment of the insertion guide device difficult. Further, in neurosurgery, a cranial drill is used to open a burr hole in the subject's skull. Variations in skull material, as well as limitations of the drilling operation can cause the burr hole location to deviate from it's ideal location, and the burr hole is not always perfectly round.

What is needed is a method and device that can be adjusted to compensate for location errors of an insertion guide device. What is also needed is a method and device that can be adjusted to compensate for location errors in forming an opening in a subject. What is also needed is a method and device that in other ways, improves accuracy and ease of use of an insertion guide device.

SUMMARY

This section provides a general summary of the disclosure, and is not a comprehensive disclosure of its full scope or all of its features.

The above mentioned problems of adjustability are addressed by the present disclosure and will be understood by reading and studying the following specification. Devices and methods are provided for adjusting an insertion guide device. The devices and methods discussed herein further offer improved accuracy and ease of use.

An insertion guide device is disclosed that guides an instrument toward a target location in a subject. The insertion guide device includes a base portion securable to the subject and an insertion guide portion defining an insertion axis. The insertion guide portion guides the instrument along the insertion axis, and the insertion guide portion is moveably supported by the base portion for movement of the insertion axis about at least two axes. Moreover, the insertion guide device includes a locking device that selectively fixes the insertion guide portion relative to the base portion to selectively fix the insertion axis relative to the at least two axes substantially concurrently.

Also, a method for guiding an instrument toward a target location in a subject is disclosed. The method includes securing a base portion to the subject and operatively supporting an insertion guide portion with the base portion. The insertion guide portion defines an insertion axis. Additionally, the method includes moving the insertion guide portion relative to the base portion and moving the insertion axis defined by the insertion guide portion about at least two axes. Moreover, the method includes concurrently fixing the insertion axis about the at least two axes and guiding the instrument along the insertion axis.

Still further, an insertion guide device for guiding an instrument through a hole in a subject toward a target location in the subject is disclosed. The hole includes an axis. The insertion guide device includes a base portion securable to the subject. The base portion includes an annular lip that extends inward. The device further includes an insertion guide portion defining a through hole that defines an insertion axis. The instrument is receivable in the through hole to be guided along the insertion axis. Moreover, the device includes a first portion fixed to the insertion guide portion. The first portion defines a slot that curves about a first axis of rotation that is positionable to be perpendicular to the axis of the hole in the subject.

Also, the device includes a second portion disposed between the first portion and the base portion, and the second portion is rotatably supported by the base portion for rotation about a second axis of rotation that is positionable to be parallel to the axis of the hole in the subject. Furthermore, the device includes a locking device that includes a gripping device, a threaded member, and a base contacting portion. The base contacting portion includes a top portion that threadably receives the threaded member and a bottom portion having a lip. The lip extends radially inward. The threaded member is moveably received in the slot of the first portion to limit rotation of the first portion and the insertion guide portion about the first axis of rotation. Upon rotating the gripping device, the threaded member is selectively and threadably advanced relative to the base contacting portion such that the lip of the base contacting portion selectively abuts the annular lip of the base portion and such that the threaded member and the base contacting portion cooperate to pull the base portion, the first portion, and the second portion together to concurrently fix the insertion axis relative to the first and second axes of rotation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
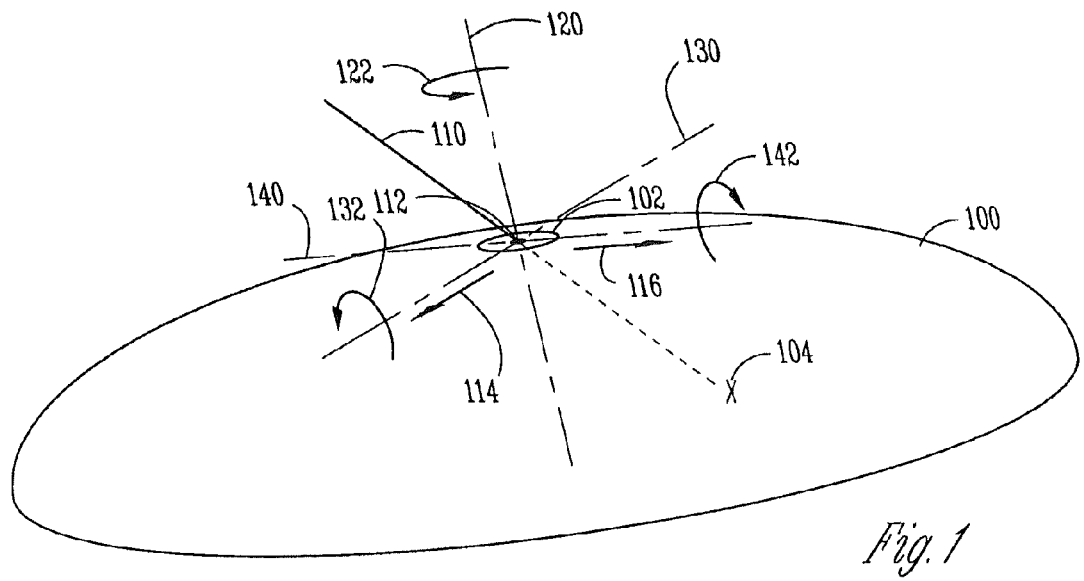
FIG. 1 shows a coordinate system in one embodiment of a neurosurgical procedure.

FIG. 1 shows a subject surface 100 along with one possible coordinate system for defining locations and orientations with respect to the subject. In one embodiment, the subject surface 100 includes a skull of a subject. An opening 102 in the subject surface is shown, along with a target location 104 within the subject. In one embodiment, the opening 102 includes a burr hole. An insertion axis 110 is shown that begins outside the subject surface 100 and ends at the target location 104. The insertion axis 110 further passes through an insertion point 112 on its way to the target location 104. The insertion point 112 is shown substantially within the center of the opening 102.

In three dimensional space, using the chosen coordinate system shown in FIG. 1, the insertion axis 110 can be rotated about the insertion point 112 and further about any of three orthogonal axes that pass through the insertion point 112. In this way, any orientation of the insertion axis 110 can be selected, while still passing through the insertion point 112. In one embodiment, rotation about at least two of the three orthogonal axes is used to select an orientation of the insertion axis 110. Although orthogonal axes are shown, non-orthogonal axes passing through the insertion point are also possible without departing from the scope of the present disclosure.

In one embodiment, a first rotational degree of freedom shown by arrow 122 is included. The first rotational degree of freedom is used for orienting the insertion axis 110. As shown, the first rotational degree of freedom rotates about a first rotational axis 120 that passes through the insertion point 112. In the embodiment shown, the first rotational axis 120 is normal to the subject surface 100 at the insertion point 112.

In one embodiment, a second rotational degree of freedom shown by arrow 132 is included. The second rotational degree of freedom is used for orienting the insertion axis 110. As shown, the second rotational degree of freedom rotates about a second rotational axis 130 that passes through the insertion point 112. In the embodiment shown, the second rotational axis 130 is tangent to the subject surface 100 at the insertion point 112.

In one embodiment, a third rotational degree of freedom shown by arrow 142 is included. The third rotational degree of freedom is used for orienting the insertion axis 110. As shown, the third rotational degree of freedom rotates about a third rotational axis 140 that passes through the insertion point 112. In the embodiment shown, the third rotational axis 140 is tangent to the subject surface 100 at the insertion point 112.

The first degree of rotational freedom, the second degree of rotational freedom, and the third degree of rotational freedom all leave the location of the insertion point 112 fixed. The degrees of rotational freedom rotate about the insertion point 112 because the location of the opening in the subject 102 remains fixed during a surgical procedure. In one embodiment, a first degree of translational freedom is also included. In one embodiment, a first degree of translational freedom is defined by the adjustability of the location of the insertion point 112 along direction 114. In one embodiment, a second degree of translational freedom is also included where the location of the insertion point 112 is adjustable along direction 116.

Figure 2:
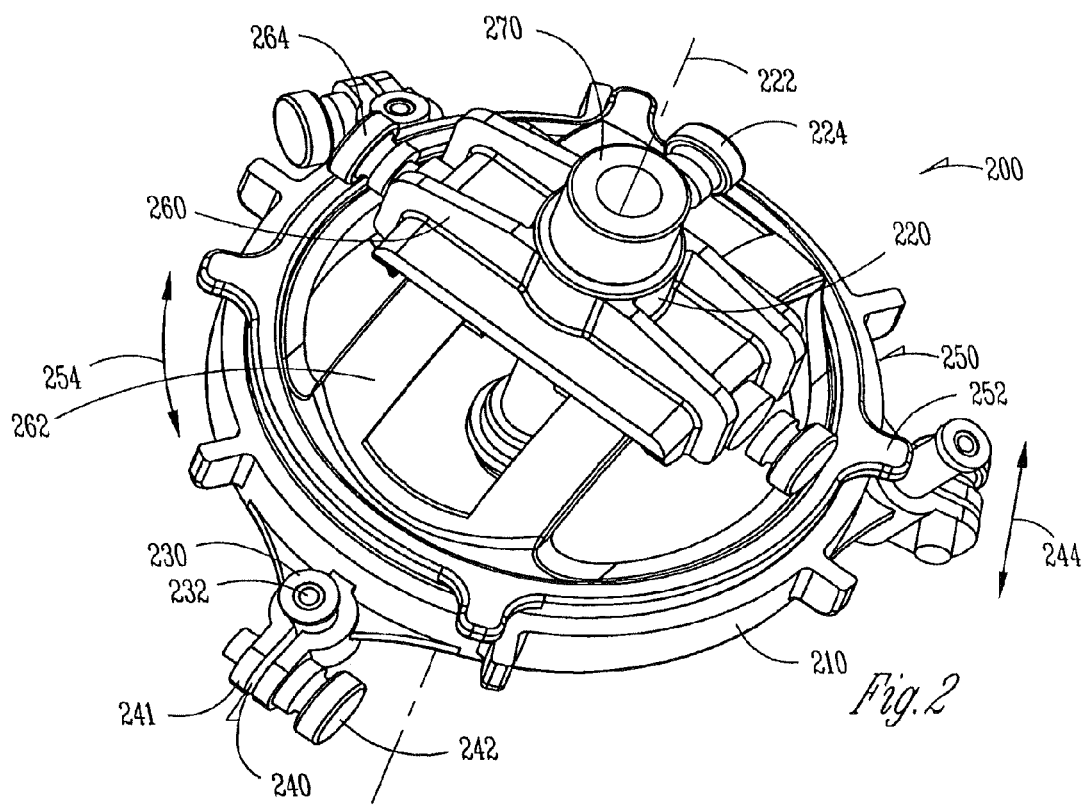
FIG. 2 shows an isometric view of an exemplary embodiment of an insertion guide device.

FIG. 2 shows one embodiment of an insertion guide device 200. The insertion guide device 200 includes a base unit 210, and an insertion guide portion 220 coupled to the base unit 210. The insertion guide portion 220 determines an insertion axis 222. A number of attachment devices 230 are also shown coupled to the base unit 210. In one embodiment, the attachment devices include a bone screw 232. The attachment devices 230 are coupled to the base unit 210 through a number of insertion point adjustment devices 240. In one embodiment, the insertion point adjustment devices 240 include a split clamping portion 241 and a screw 242. The insertion point adjustment devices 240 allow the base unit to be adjusted with respect to the attachment devices 230 substantially along direction 244. In one embodiment an insertion point adjustment device 240 is included for each attachment device 230. In one embodiment, the insertion guide device 200 includes three attachment devices 230 and three insertion point adjustment devices 240.

By adjusting at least one insertion point adjustment devices 240, an insertion point (not shown) of the insertion axis 222 is translated through at least one degree of translational freedom to a selected location within the subject surface. Three attachment devices are convenient because they provide the most stable platform with a minimum number of contact points on the subject.

FIG. 2 also shows a first angular adjustment device 250 for adjusting a first rotational degree of freedom. The first angular adjustment device 250 permits rotation of a component of the insertion axis 222 about a first rotational axis that is substantially normal to the subject surface at the insertion point. The rotation of the insertion axis 222 in the first rotational degree of freedom is shown by arrows 254. A locking device 252 is shown to secure an orientation of the insertion axis 222 in the first rotational degree of freedom as selected. In one embodiment, the locking device includes a threaded lock ring.

Also shown in FIG. 2 is a second angular adjustment device 260 for adjusting a second rotational degree of freedom. The second angular adjustment device 260 permits rotation of the insertion axis 222 about the insertion point and further about a second rotational axis. In one embodiment, the second rotational axis is substantially tangent to the subject surface at the insertion point. In one embodiment, the second angular adjustment device 260 includes a rail 262 that guides the adjustment of the second angular adjustment device 260. In one embodiment, a pair of rails 262 are used. In one embodiment, a locking device 264 is used to secure an orientation of the insertion axis 222 in the second rotational degree of freedom as selected. In one embodiment, the locking device 264 includes one or more set screws.

A centering guide 270 is further shown in FIG. 2. In one embodiment, the centering guide is fixed within the insertion guide portion 220 using a locking device 224. In one embodiment, the locking device 224 includes one or more set screws. Embodiments of the centering guide are discussed in more detail later in the specification.

In one embodiment, selected elements of an insertion guide device such as insertion guide device 200 are fabricated from a substantially transparent material. Examples of transparent materials include, but are not limited to, polycarbonate, crystalline polymers, glasses, etc. An advantage of at least some of the elements of an insertion guide device being transparent is that it allows a user or surgeon to better view the opening in the subject, and to view within the opening into the subject. In many procedures, it is important to be able to view the opening in the subject, and further to view locations within the opening. Embodiments of insertion guide devices as described in this document are mounted to the subject at locations that are spaced laterally apart from the opening, thus providing a user or surgeon a better view of the opening. By further designing elements of an insertion guide device with substantially transparent material, a surgeon's ability to see the opening and inside the opening is increased.

Figure 3:
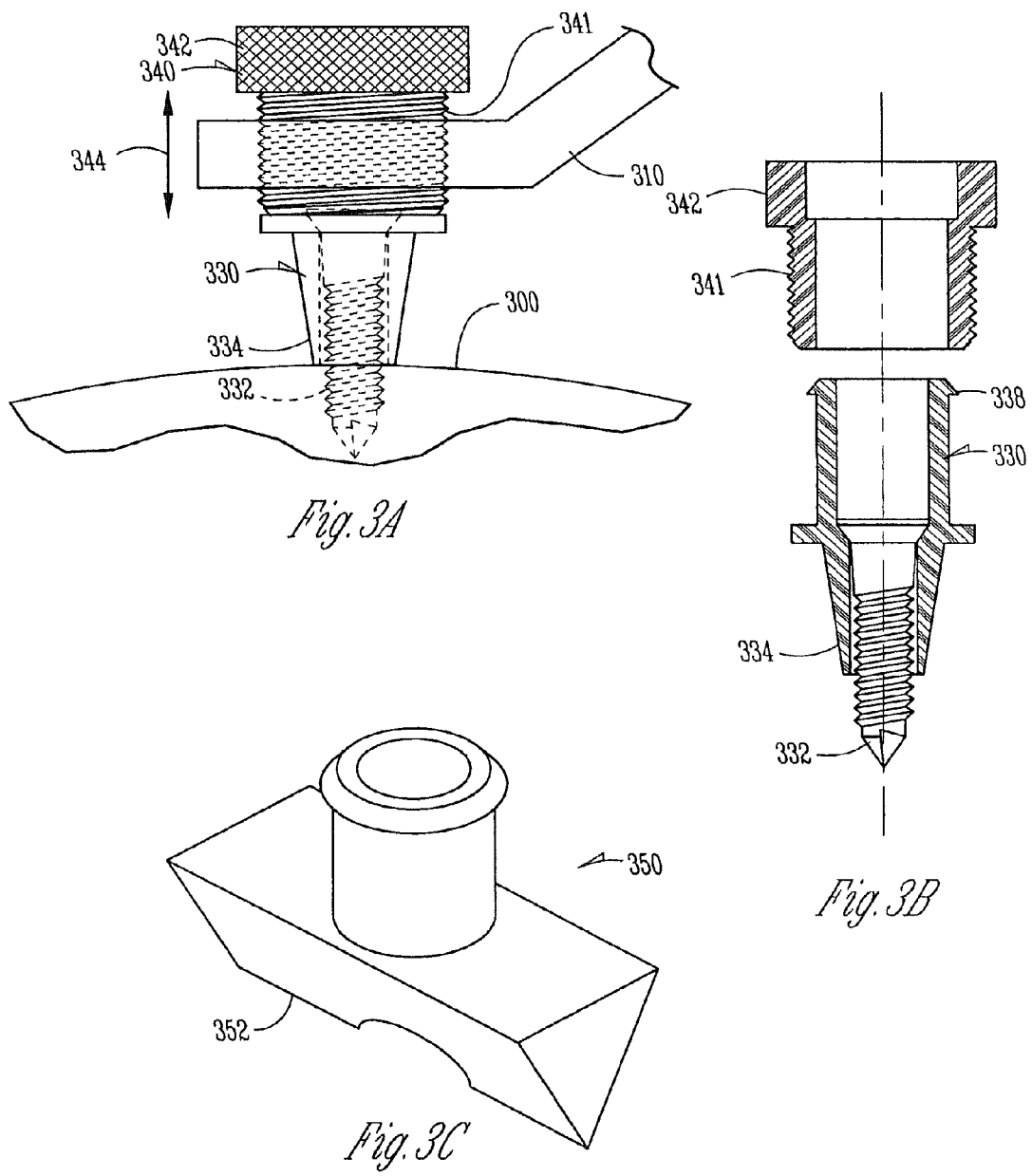
FIG. 3A shows a side view of a portion of an exemplary embodiment of an insertion guide device.
FIG. 3B shows a cross section view of a portion of an exemplary embodiment of an insertion guide device.
FIG. 3C shows an isometric view of a part of an exemplary embodiment of an insertion guide device.

FIG. 3A shows an embodiment of an attachment device 330 and an insertion point adjustment devices 340 attached to a subject surface 300. In one embodiment, the attachment device 330 includes a truncated cone portion 334 and a securing device 332 such as a bone screw. In one embodiment, the insertion point adjustment devices 340 includes a threaded portion 341 coupled to a gripping portion 342. In one embodiment, the gripping portion 342 includes a knurled knob portion. In one embodiment, the threaded portion 341 engages a portion of a base 310 to provide motion of the base 310 substantially along directional arrows 344 with respect to the attachment device 330.

FIG. 3B shows a cross section of the attachment device 330 and an insertion point adjustment devices 340 of FIG. 3A. In one embodiment, the threaded portion 341 and the gripping portion 342 are separately fabricated from the attachment device 330. In one embodiment, the threaded portion is rotatably coupled to the attachment device 330 by a retaining device 338. In one embodiment, the retaining device 338 includes a barb. A rotatably coupled arrangement allows the attachment device 330 to remain substantially fixed while adjustments are made to the threaded portion 341.

FIG. 3C shows an embodiment of an attachment device 350 including a substantially linear contact surface 352. In one embodiment, features such as the substantially linear contact surface 352 and the truncated cone portion 334 help to reduce tissue damage due to attachment of the insertion guide device to a subject.

During many surgical procedures utilizing attached devices such as an insertion guide device, tissue damage as a result of attachment is an issue. In one embodiment, tissue damage is reduced by utilizing a minimum number of attachment devices. In one embodiment, three attachment devices are used to maintain a stable platform for the insertion guide device while minimizing a number of attachment locations. In one embodiment, the attachment devices are located apart from the opening in the subject, such as a burr hole. The more remote location of attachment devices reduces tissue damage at the opening or burr hole location. In one embodiment, the attachment devices raise a substantial portion of the insertion guide device above the subject surface. By raising the insertion guide device above the subject surface, tissue damage due to pinching large amounts of tissue under the insertion guide device is avoided.

In one embodiment, the shape of the attachment device or devices further reduces tissue damage. In one embodiment the truncated cone shape reduces a subject contact surface to a minimum area where sufficient support for the securing device such as a bone screw is provided, while reducing the contact area. In one embodiment, a cone shape is desirable due to the use of a round cutting device to pierce tissue on a subject's scalp prior to attachment. In one embodiment, a modified hypodermic needle is used to pierce the scalp, thus making a round attachment device convenient. In one embodiment, a substantially linear contact surface is desirable due to the use of a linear cutting instrument to pierce tissue on a subject's scalp prior to attachment. In one embodiment, a scalpel is used to pierce the scalp, thus making a substantially linear contact surface of an attachment device convenient.

Figure 4:
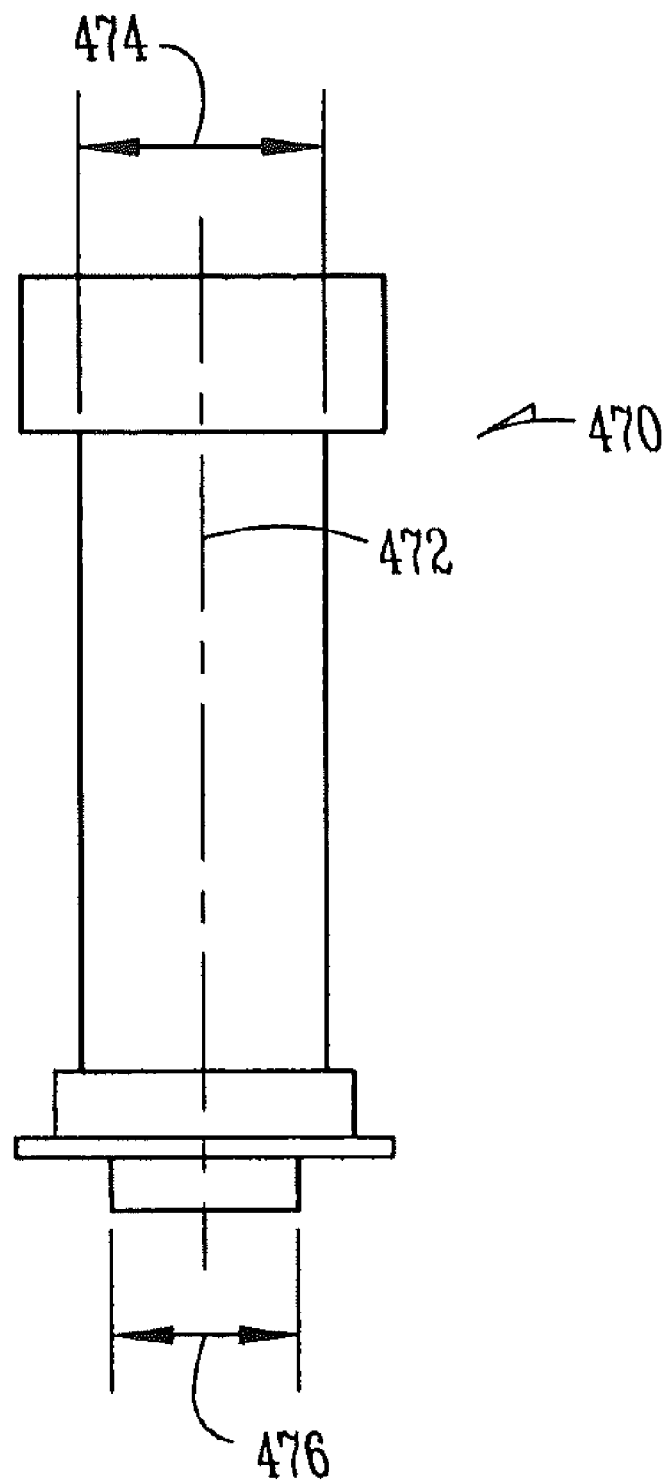
FIG. 4 shows a side view of an exemplary embodiment of a centering guide.

FIG. 4 shows one embodiment of a centering device 470 similar to the embodiment illustrated in FIG. 2. The device configuration and use of a centering device is not, however, limited to the embodiment illustrated in FIG. 2. The centering device 470 includes an insertion axis 472, a first diameter portion 474 and a second diameter portion 476. In one embodiment, the first diameter portion 474 forms a close tolerance fit within an insertion guide portion so that the insertion axis 472 can be adjusted using adjustable features of the insertion guide device embodiments as described above. In one embodiment, the second diameter portion 476 forms a close tolerance fit within an opening in a subject such as a burr hole. In one embodiment, the second diameter portion 476 fits inside an irregular opening in a subject such as a burr hole to effectively find an approximate center of an irregular opening.

In a surgical procedure, such as neurosurgery, after installation of an insertion guide device, an insertion point may not be aligned over the center of a round burr hole, or the effective center of an irregular burr hole. In one embodiment, the translational location of the insertion point can be adjusted using insertion point adjustment devices as described above. In one embodiment, a centering guide can be further utilized to indicate to a user when the insertion point is aligned with the center of the opening in the subject. In one embodiment, when the insertion point has been moved such that the second diameter portion 476 fits at least partially within the opening in the subject, the insertion point is aligned with the opening in the subject.

In one embodiment, a centering device is used to center an insertion point of an insertion guide device over an opening in a subject prior to attachment of the insertion guide device on the subject. The centering device allows a fast and efficient location of attachment points for the insertion guide device in embodiments where the location of attachment points has not already been determined.

Figure 5A:
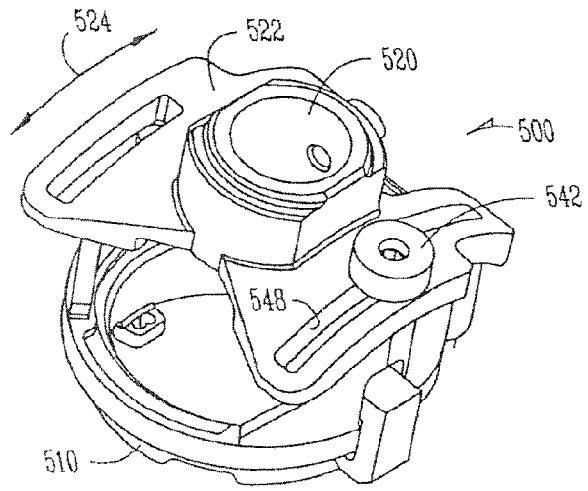
FIG. 5A shows an isometric view of a portion of an exemplary embodiment of an insertion guide device.

FIG. 5A shows a portion of an insertion guide device 500. In one embodiment, attachment devices and insertion point adjustment devices as described above are used in conjunction with embodiments described in FIGS. 5A-5C. An insertion guide portion 520 is shown coupled to a first portion 522. The insertion guide portion 520 is further coupled to a second portion 530. The insertion guide portion 520 is further coupled to a base portion 510. A first angular adjustment device is shown in FIG. 5A that permits rotation adjustment of an insertion axis 502 along direction 524. A second angular adjustment device is shown in FIG. 5B that permits rotation adjustment of an insertion axis 502 along direction 526.

In one embodiment, the portion of an insertion guide device 500 includes a locking device 540 that fixes both the first angular adjustment device and the second angular adjustment device concurrently when actuated. In one embodiment, the locking device 540 includes a gripping device 542 such as a knob. In one embodiment, the locking device 540 includes a threaded member 544 coupled to the gripping device 542. In one embodiment, the threaded member 544 passes through a slot 548 in the first portion 522, allowing the first portion to move along direction 524 with respect to the body portion 510. In one embodiment, the locking device 540 includes a base contacting portion 546. The base contacting portion 546 can include a contacting lip 547 that extends radially inward (FIG. 5C). Also, the base portion 510 can include a base lip 549 that extends radially outward (FIG. 5C) to abut with the contacting lip 547.

Figure 5B:
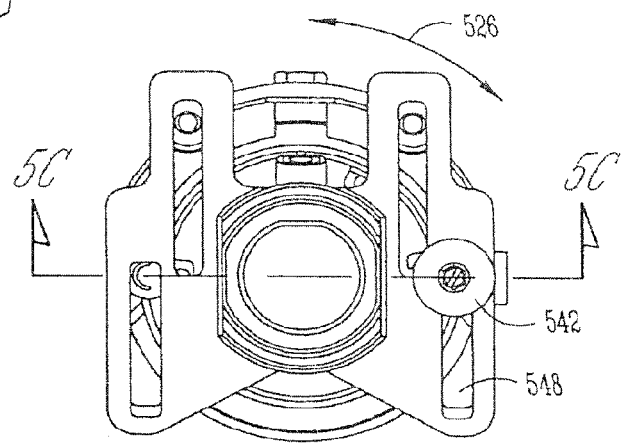
FIG. 5B shows a top view of a portion of an exemplary embodiment of an insertion guide device.
Figure 5C:
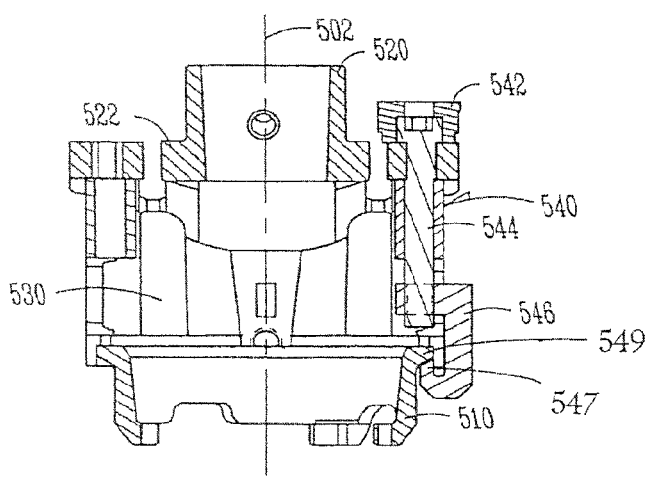
FIG. 5C shows a cross section view taken along line 5C-5C of FIG. 5B.

In operation, the embodiment shown in FIGS. 5A-5C fixes an orientation of the insertion axis 502 in multiple degrees of freedom concurrently by tightening the threaded member 544 with the gripping portion 542. The threaded member in turn tightens the base contacting portion 546 against the base 510. This tightening motion pulls the base 510; the first portion 522, and the second portion 530 together, substantially fixing their respective locations.

Using one locking device 540 to fix multiple adjustment devices is desirable in one embodiment because it allows a surgeon to quickly and easily secure all movement of an insertion axis 502 in a single locking operation once a desired orientation is found. A tradeoff is also present, in that during some operations, precise adjustment requires that each degree of freedom, or angular adjustment is focused on independently. When independent focus on each degree of freedom is necessary, individual angular adjustment and individual locking devices are desirable.

Figure 5D:
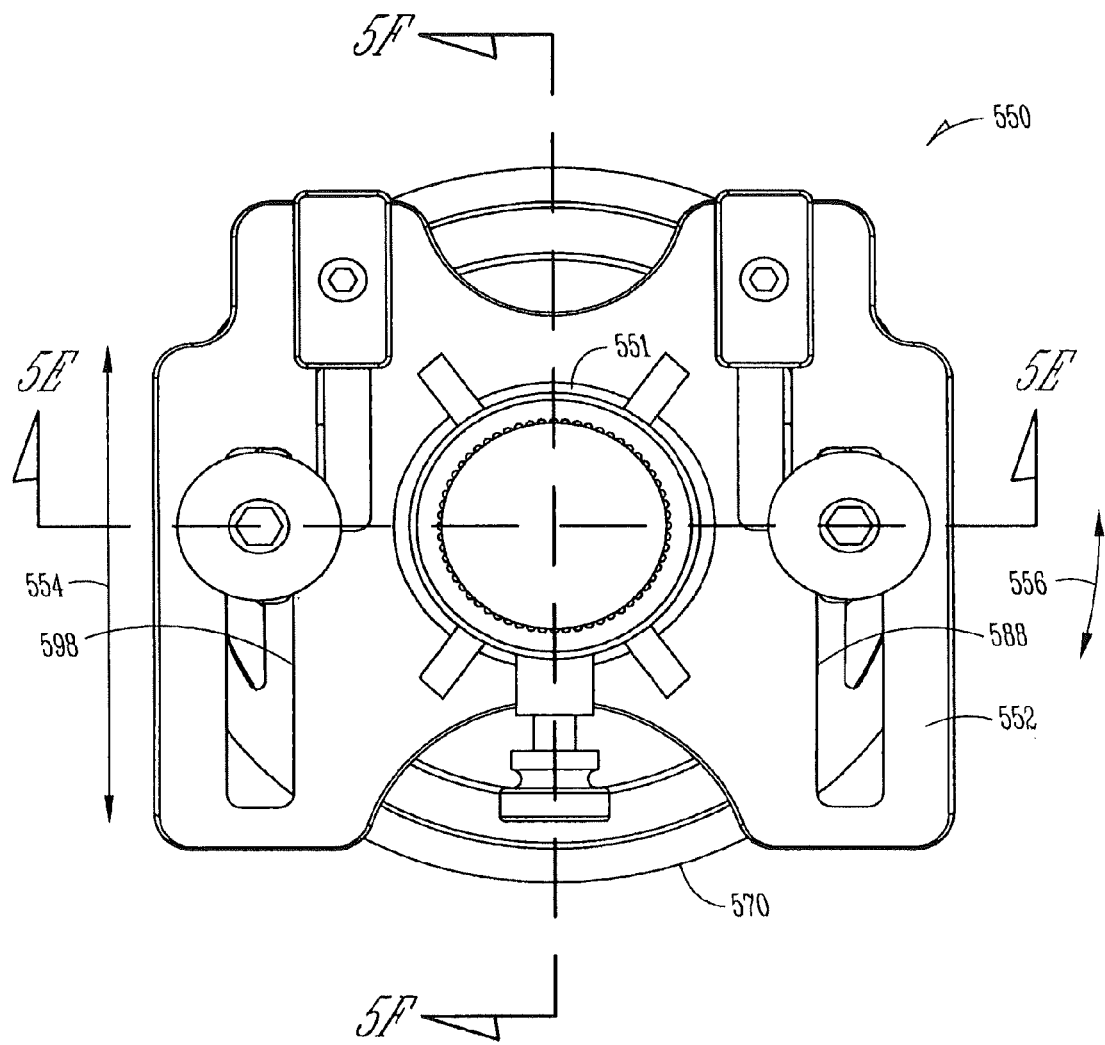
FIG. 5D shows a top view of a portion of an exemplary embodiment of an insertion guide device.
Figure 5E:
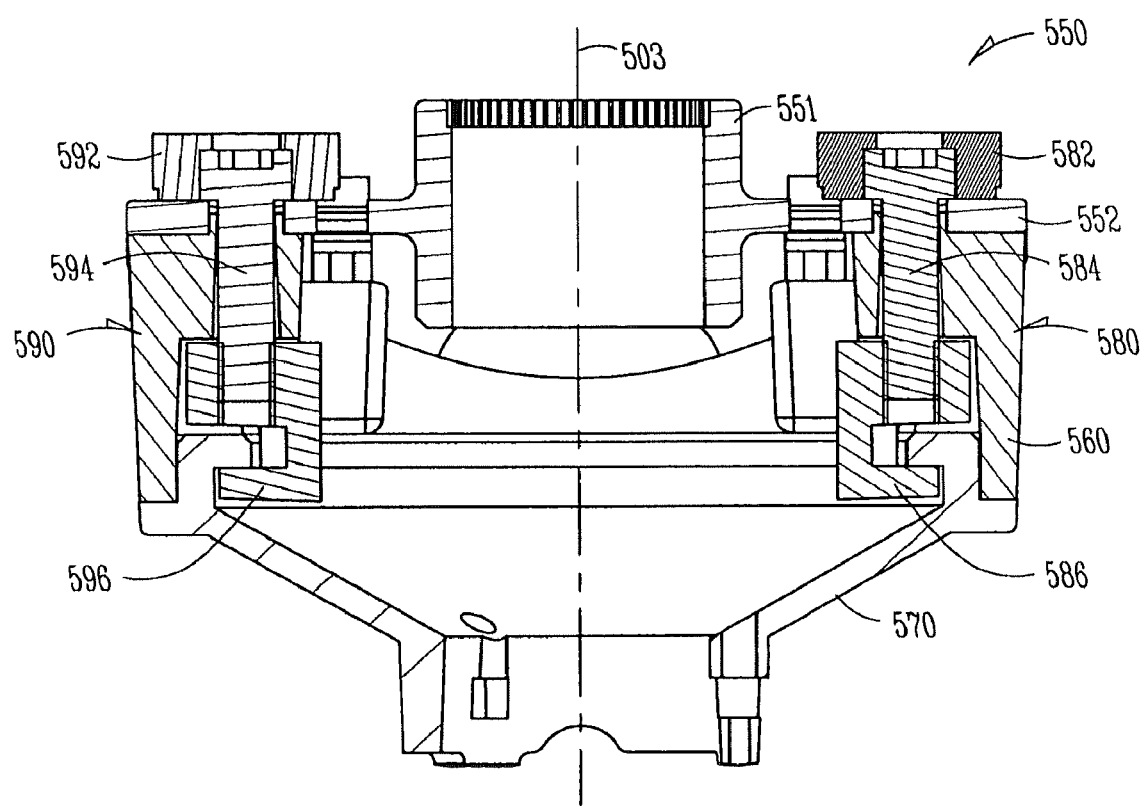
FIG. 5E shows a cross section view taken along line 5E-5E of FIG. 5D.
Figure 5F:
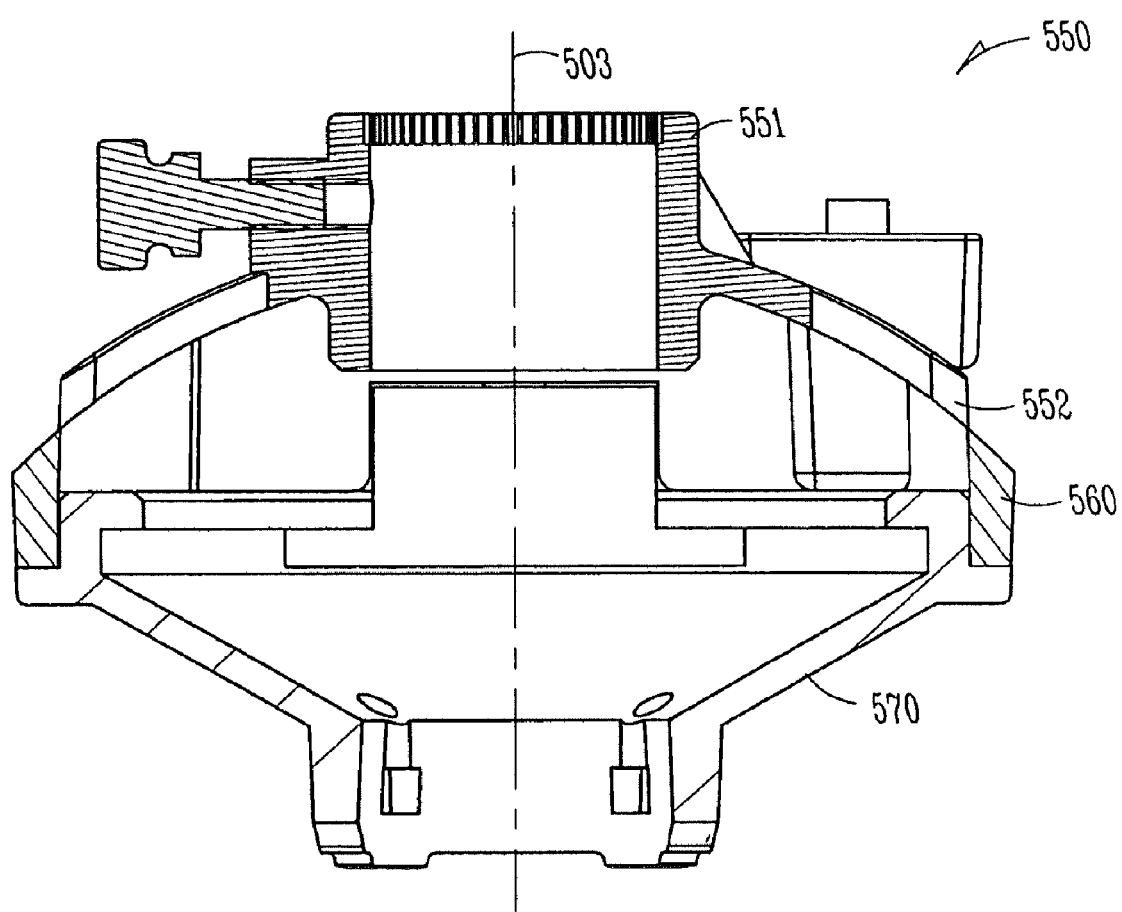
FIG. 5F shows a cross section view taken along line 5F-5F of FIG. 5D.

An additional embodiment is shown in FIGS. 5D-F. FIG. 5D shows a portion of an insertion guide device 550. In one embodiment, attachment devices and insertion point adjustment devices as described above are used in conjunction with embodiments described in FIGS. 5D-5F. An insertion guide portion 551 is shown coupled to a first portion 552. The insertion guide portion 551 is further coupled to a second portion 560. The insertion guide portion 551 is further coupled to a base portion 570. A first angular adjustment device is shown in FIG. 5D that permits rotation adjustment of an insertion axis 503 along direction 554. A second angular adjustment device is shown in FIG. 5D that permits rotation adjustment of an insertion axis 503 along direction 556.

In one embodiment, the portion of an insertion guide device 551 includes a locking device 580 that fixes both the first angular adjustment device and the second angular adjustment device concurrently when actuated. In one embodiment, the locking device 580 includes a gripping device 582 such as a knob. In one embodiment, the locking device 580 includes a threaded member 584 coupled to the gripping device 582. In one embodiment, the threaded member 584 passes through a slot 588 in the first portion 552, allowing the first portion 552 to move along direction 554 with respect to the body portion 570. In one embodiment, the locking device 580 includes a base contacting portion 586.

In operation, the embodiment shown in FIGS. 5D-5F fixes an orientation of the insertion axis 503 in multiple degrees of freedom concurrently by tightening the threaded member 584 with the gripping portion 582. The threaded member in turn tightens the base contacting portion 586 against the base 570. This tightening motion pulls the base 570; the first portion 552, and the second portion 560 together, substantially fixing their respective locations.

In one embodiment, the portion of an insertion guide device 551 includes a second locking device 590 that fixes both the first angular adjustment device and the second angular adjustment device concurrently when actuated. In one embodiment, the locking device 590 includes a gripping device 592 such as a knob. In one embodiment, the locking device 590 includes a threaded member 594 coupled to the gripping device 592. In one embodiment, the threaded member 594 passes through a slot 598 in the first portion 552, allowing the first portion 552 to move along direction 554 with respect to the body portion 570. In one embodiment, the locking device 590 includes a base contacting portion 596.

One advantage of designs shown in FIGS. 5D-F includes the ability to quickly and easily secure all movement of an insertion axis 503 in a single locking operation once a desired orientation is found. An additional locking device, such as locking device 590 provides extra security that the degrees of freedom of the insertion guide device 551 will not accidentally move out of the selected alignment.

Figure 6A:
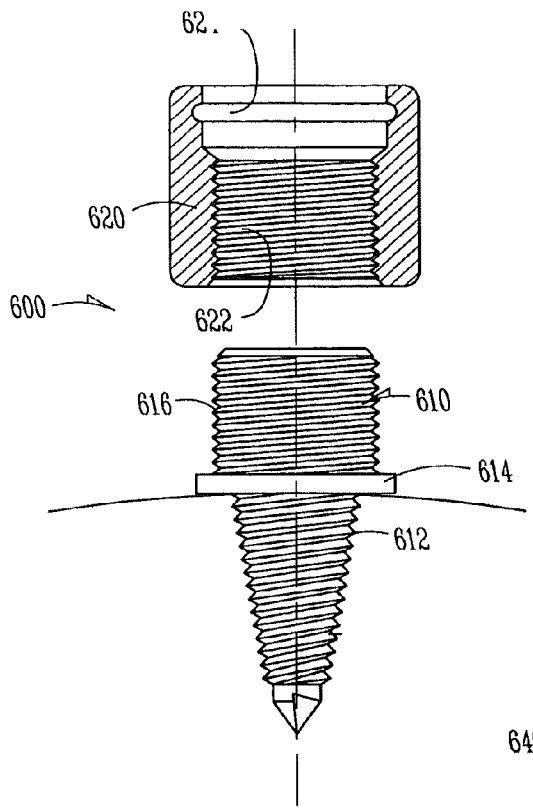
FIG. 6A shows a cross section view of a portion of an exemplary embodiment of a fiducial marker.

FIGS. 6A-6D show a number of embodiments of fiducial markers and portions of fiducial markers according to embodiments of the invention. In FIG. 6A, a securing device 610 is shown with a subject securing portion 612, a transition portion 614, and an upper securing portion 616. In one embodiment, the subject securing portion includes a bone screw portion. In one embodiment, the upper securing portion includes a threaded portion.

An interchange portion 620 is also shown in FIG. 6A. In one embodiment, the interchange portion 620 includes a mating portion 622 that engages the upper securing portion 616 of the securing device 610. In one embodiment, the mating portion 622 includes a mating threaded portion. Also shown is a holding region 624 such as a groove.

Figure 6B:
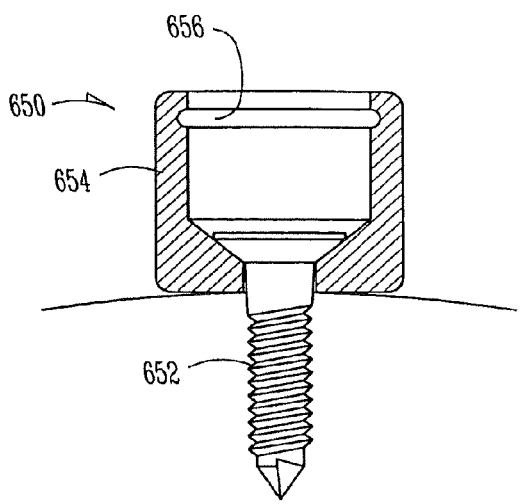
FIG. 6B shows a cross section view of a portion of an exemplary embodiment of a fiducial marker.

FIG. 6B shows an embodiment of a portion of a fiducial marker 650. A subject securing device 652, such as a more conventional bone screw, is shown attaching an interchange portion 654 to a subject surface. Similar to FIG. 6A, a holding region 656 such as a groove is shown coupled to the interchange portion 654. In one embodiment, the use of a more conventional bone screw is more cost effective in manufacturing of the portion of the fiducial marker 650.

Figure 6C:
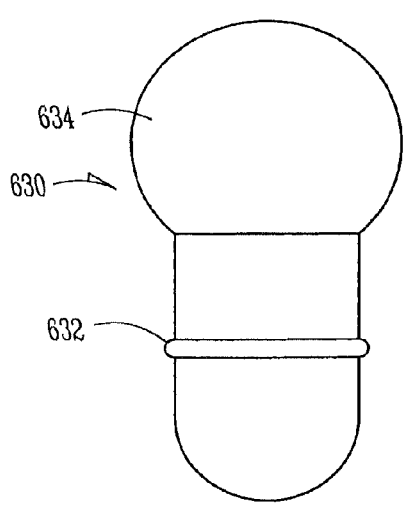
FIG. 6C shows a portion of an exemplary embodiment of a fiducial marker.

FIG. 6C shows an interchangeable indicator 630. The interchangeable indicator 630 includes an upper portion 634 that functions to indicate a point location in a medical imaging device such as a CT or MRI device, etc. In one embodiment, the upper portion reflects a selected wavelength of light that in turn indicates a position of a portion of a subject, using a detection device. A mating portion 632 is further shown attached to the upper portion 634. The mating portion 632 is adapted to be removably positioned within a holding region such as the holding regions 624 and 656 described above.

Figure 6D:
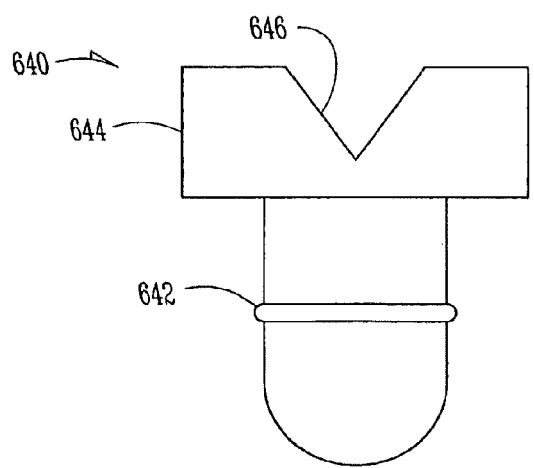
FIG. 6D shows a portion of an exemplary embodiment of a fiducial marker.

FIG. 6D shows an adaptor device 640 for use with embodiments of the insertion guide device as described above. In one embodiment, the interchangeable indicator 630 is adapted to be removed after initial subject imaging is complete. The adaptor device 640 may then be inserted into an embodiment of the fiducial markers or portions of fiducial markers as described above. In one embodiment, the insertion guide device is then directly mountable to the fiducial markers or portions of fiducial markers without additional attachments needed. Tissue damage, as discussed above, is reduced using this configuration, as well as increased targeting accuracy due to the use of the exact fiducial locations to mount the insertion guide device.

In one embodiment, the adaptor device 640 includes an upper portion 644 with a receiving portion 646. The receiving portion is adapted to couple with attachment devices of insertion guide devices as described above. In one embodiment, the receiving portion includes a groove, although the present disclosure is not so limited. Although an adaptor device is shown in FIG. 6D for use in coupling an insertion guide device to a number of fiducial markers or portions of a number of fiducial markers, the present disclosure is not so limited. The insertion guide device may also be directly attached to a number of fiducial markers or portions of a number of fiducial markers directly without use of an adaptor device.

Figure 7:
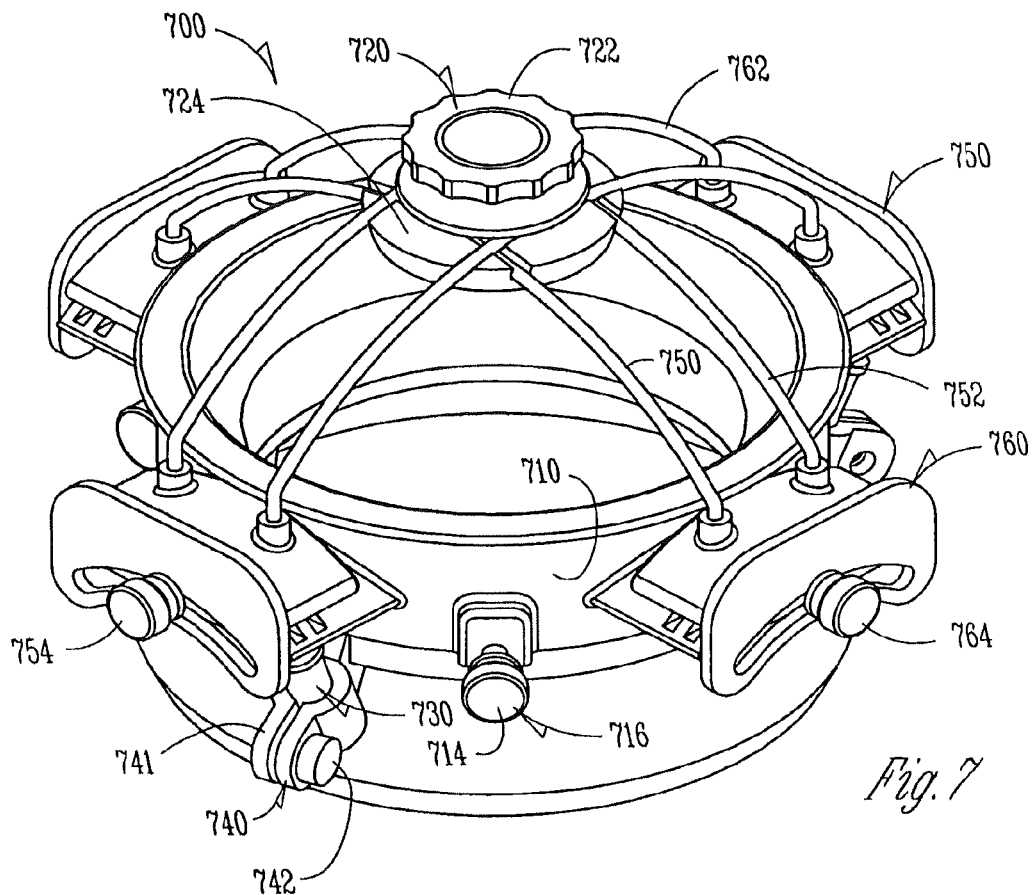
FIG. 7 shows an isometric view of an exemplary embodiment of an insertion guide device.

FIG. 7 shows an embodiment of an insertion guide device 700. The insertion guide device 700 includes a base unit 710, and an insertion guide portion 720 coupled to the base unit 710. The insertion guide portion 720 determines an insertion axis similar to embodiments shown above. A number of attachment devices 730 are also shown coupled to the base unit 710. The attachment devices 730 are coupled to the base unit 710 through a number of insertion point adjustment devices 740. In one embodiment, the insertion point adjustment devices 740 include a split clamping portion 741 and a screw 742. The insertion point adjustment devices 740 allow the base unit 710 to be adjusted with respect to the attachment devices 730 similar to embodiments discussed above. In one embodiment an insertion point adjustment device 740 is included for each attachment device 730. In one embodiment, the insertion guide device 700 includes three attachment devices 730 and three insertion point adjustment devices 740. By adjusting at least one insertion point adjustment devices 740, an insertion point (not shown) is translated through at least one degree of translational freedom to a selected location within the subject surface.

FIG. 7 also shows a first angular adjustment device 750 for adjusting a first rotational degree of freedom. The first angular adjustment device 750 permits rotation of a component of the insertion axis about a first rotational axis. In one embodiment, the first rotational axis is substantially tangent to the subject surface at the insertion point. In one embodiment, at least one rail 752 guides the insertion guide portion 720 along the first rotational degree of freedom. A locking device 754 is shown to secure an orientation of the insertion axis in the first rotational degree of freedom as selected. In one embodiment, the locking device includes at least one set screw.

FIG. 7 also shows a second angular adjustment device 760 for adjusting a second rotational degree of freedom. The second angular adjustment device 760 permits rotation of a component of the insertion axis about a second rotational axis. In one embodiment, the second rotational axis is substantially tangent to the subject surface at the insertion point. In one embodiment, at least one rail 762 guides the insertion guide portion 720 along the second rotational degree of freedom. A locking device 764 is shown to secure an orientation of the insertion axis in the first rotational degree of freedom as selected. In one embodiment, the locking device includes at least one set screw.

FIG. 7 also shows a third angular adjustment device 716 for adjusting a third rotational degree of freedom. The third angular adjustment device 716 permits rotation of a component of the insertion axis about a third rotational axis. In one embodiment, the third rotational axis is substantially normal to the subject surface at the insertion point. In one embodiment, a rotating body portion 712 is allowed to rotate with respect to the body 710. A locking device 714 is shown to secure an orientation of the insertion axis in the third rotational degree of freedom as selected. In one embodiment, the locking device includes at least one set screw.

In one embodiment, the insertion guide portion 720 includes a locking device 722. In one embodiment the locking device 722 includes a knob attached to a threaded portion that bears down against a back plate 724. In one embodiment at least two of the rotational degrees of freedom of the insertion guide device 700 can be concurrently fixed using the locking device 722. In one embodiment, the first rotational degree of freedom and the second rotational degree of freedom can be concurrently fixed using the locking device 722. FIG. 7 shows an embodiment where the rails 752 and rails 762 are fixed between the locking device 722 and the back plate 724 upon actuation of the locking device 722.

Figure 8:
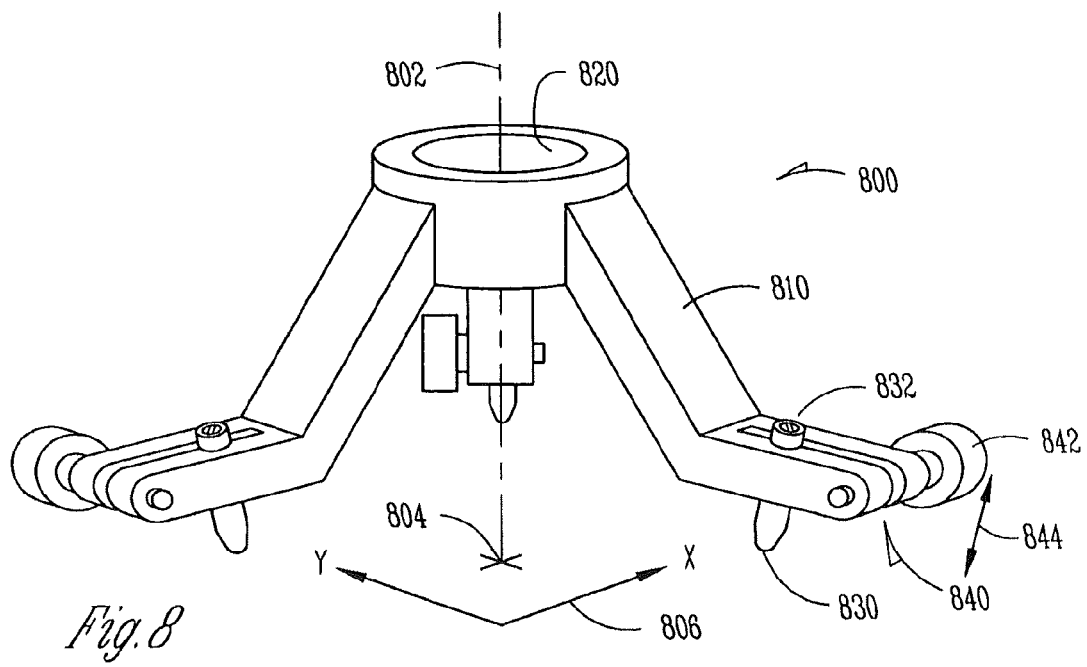
FIG. 8 shows an isometric view of an exemplary embodiment of an insertion guide device.

FIG. 8 shows one embodiment of an insertion guide device 800. The insertion guide device 800 includes a base unit 810, and an insertion guide portion 820 coupled to the base unit 810. The insertion guide portion 820 determines an insertion axis 802 similar to embodiments shown above. A number of attachment devices 830 are also shown coupled to the base unit 810. In one embodiment, the attachment devices 830 include a bone screw 832. The attachment devices 830 are coupled to the base unit 810 through a number of insertion point adjustment devices 840. In one embodiment, the insertion point adjustment devices 840 include a split clamping portion and a screw 842.

The insertion point adjustment devices 840 allow the base unit 810 to be adjusted with respect to the attachment devices 830 similar to embodiments discussed above. In one embodiment, the insertion point adjustment devices 840 allow the base unit 810 to be adjusted with respect to the attachment devices 830 substantially along direction 844. In one embodiment an insertion point adjustment device 840 is included for each attachment device 830. In one embodiment, the insertion guide device 800 includes three attachment devices 830 and three insertion point adjustment devices 840.

By adjusting at least one insertion point adjustment device 840, an insertion point 804 is translated through at least one degree of translational freedom to a selected location within the subject surface. In one embodiment, the insertion point 804 is adjustable in both an X-axis and a Y-axis as shown by coordinate axes 806.

In one embodiment, the insertion guide device 800 does not include any adjustment about rotational degrees of freedom as described above. In one embodiment, an orientation of the insertion axis 802 is pre-determined upon fabrication of the body 810 and the insertion guide portion 820. In one embodiment, the insertion guide device 800 is custom fabricated using stereolithography rapid prototyping or other suitable custom fabrication techniques.

Figure 9:
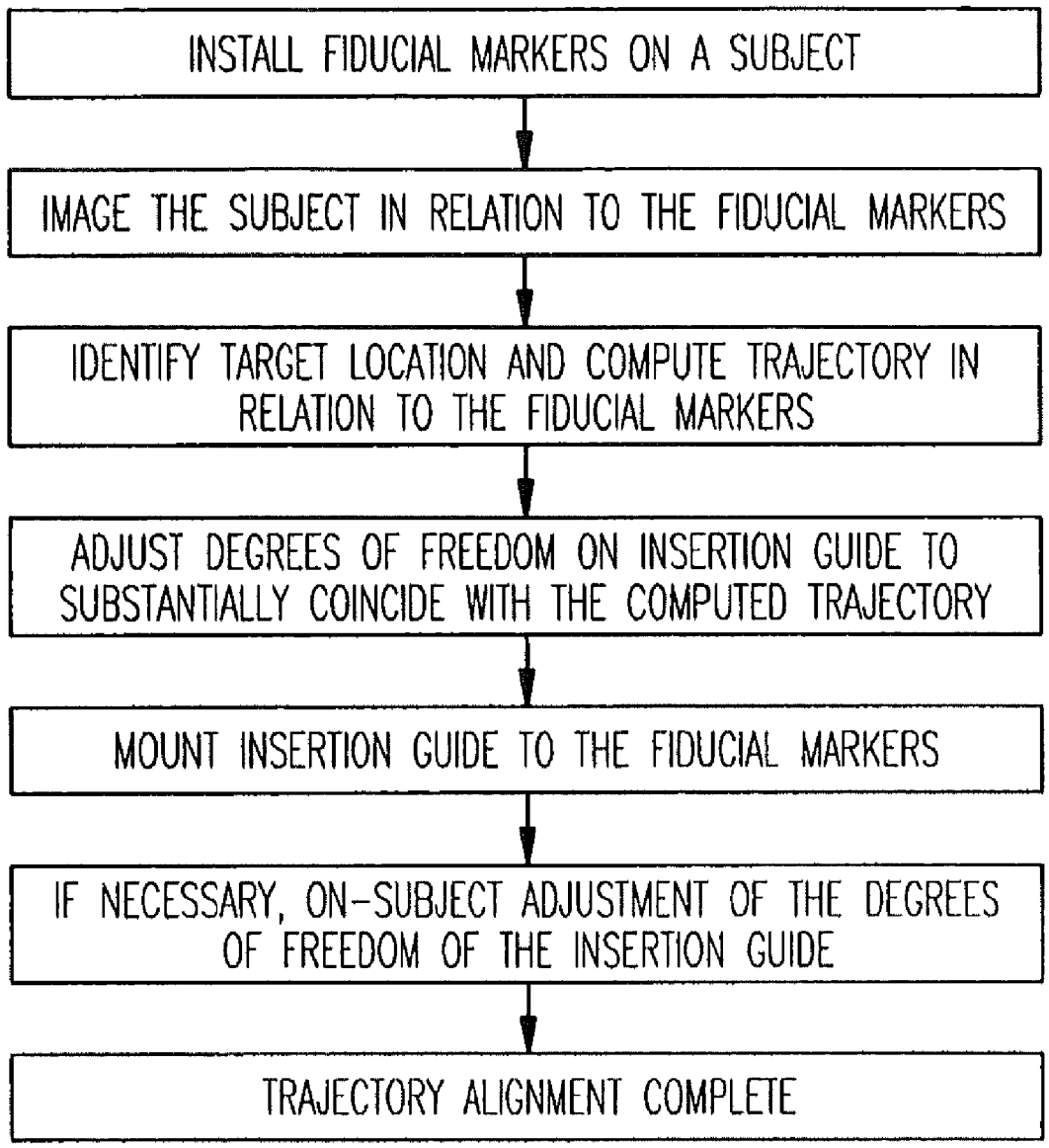
FIG. 9 shows a flow diagram of an exemplary embodiment of a method according to various teachings of the present disclosure.

FIG. 9 shows a flow diagram of one method of aligning an insertion guide using embodiments of the invention as described above. As shown in FIG. 9, fiducial markers are first installed on a subject, such as a surgical patient. The subject is then imaged using imaging techniques as described above, such as CT or MRI techniques, etc. An image is generated of the subject with tissue shown in relation to the fiducial markers, which are concurrently imaged using the selected imaging technique. The target location within the subject is determined, and a trajectory is computed between a location external to the subject, to the target location.

An embodiment of an insertion guide device is then adjusted using degrees of freedom as described in embodiments above, to substantially coincide with the computed trajectory in relation to the fiducial markers. In one embodiment, attachment devices and corresponding insertion point adjustment devices are asymmetrically spaced about a circumference of the base unit of the insertion guide device to provide easy orientation of the insertion guide on the fiducial markers.

The insertion guide device is then attached to the fiducial markers in a state of substantial alignment with the desired trajectory as determined by imaging. One advantage of a method as described above, is that substantial alignment of the insertion guide is possible without the subject being present. This allows time in the operating room to be reduced. Optionally, alignment of the insertion guide can be performed on the subject. Although substantial alignment of the insertion guide device can be accomplished without the subject being present, it is sometimes necessary to perform fine adjustment with the insertion guide device attached on the subject. As described previously, variations in mounting an insertion guide device or opening a burr hole can make fine adjustments necessary.

Although particular orders of operations in the method described above are discussed, one of ordinary skill in the art, with the benefit of the present specification will recognize that other orders of operation are possible without departing from the invention.

CONCLUSION

Thus, an insertion guide has been shown that includes at least one insertion point adjustment device. Using embodiments of an insertion guide device as described above, a user such as a surgeon is able to adjust a lateral position of an insertion point to more precisely center the insertion point within an opening in a subject, such as a burr hole. Selected embodiments described above further include a centering guide that easily indicates to a user when the insertion point is substantially centered within the opening in the subject.

Selected embodiments described above further include adjustments of rotational degrees of freedom of an insertion axis. These adjustments allow a user to align the insertion axis with a target location within a subject, without changing the lateral (translational) location of the insertion point. Selected embodiments described above permit a user to fix multiple degrees of rotational freedom using a single locking device.

Selected embodiments described above further include the ability to attach an insertion guide device to at least one existing fiducial marker. The ability to attach to a fiducial marker improves accuracy of the insertion guide device by aligning more precisely with imaged locations on a subject, and tissue damage or other attachment surface damage is reduced by eliminating a separate attachment procedure for the insertion guide device, apart from the attachment of the fiducial markers.

Selected embodiments described above further include attachment of a large percentage of an insertion guide device at a distance above a subject surface. Reducing a contact surface area reduces tissue damage or other attachment surface damage due to an attachment procedure. Embodiments utilizing substantially transparent materials increase viewability of an opening in a subject.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present disclosure. It is to be understood that the above description is intended to be illustrative, and not restrictive. Combinations of the above embodiments, and other embodiments will be apparent to those of skill in the art upon reviewing the above description. The scope of the present disclosure includes any other applications in which the above structures and fabrication methods are used. The scope of the present disclosure should be determined with reference to the appended claims, along with the full scope of equivalents to which such claims are entitled.

What is claimed is:

1. An insertion guide device for guiding an instrument toward a target location in a subject, the insertion guide device comprising:
   a base portion securable to the subject;
   a second portion that is rotatably attached to the base portion for rotation relative to the base portion about a second axis of rotation;
   a first portion that is rotatably attached to the second portion for rotation relative to the second portion about a first axis of rotation;
   an insertion guide portion defining an insertion axis, the insertion guide portion fixed to the first portion, the insertion guide portion guiding the instrument along the insertion axis, the insertion axis being rotatable about both the first and second axes to be disposed at a positive angle relative to both the first and second axes; and a locking device that selectively fixes the insertion guide portion relative to the base portion to fix the insertion axis relative to the first and second axes substantially concurrently.

2. The insertion guide device of claim 1, wherein the subject includes an opening that defines an axis, wherein the base portion is securable to the subject such that the second axis of rotation is substantially parallel to the axis of the opening, and wherein the first axis of rotation is perpendicular to the second axis of rotation.

3. The insertion guide device of claim 1, wherein the second portion is disposed between the first portion and the base portion.

4. The insertion guide device of claim 1, wherein the first portion defines a slot having a curved axis, and wherein the locking device includes a member that is moveably received in the slot, the slot limiting rotation of the first portion about the first axis.

5. The insertion guide device of claim 1, wherein the locking device includes a base contacting portion that selectively abuts against the base portion to selectively retain the second portion against rotation about the second axis.

6. The insertion guide device of claim 1, wherein the locking device includes a pulling member and a base contacting portion, the base contacting portion selectively engaging the base portion, the second portion disposed between the first portion and the base contacting portion, the pulling member and the base contacting portion cooperating to selectively pull the base portion, the first portion, and the second portion together to selectively fix the insertion axis relative to the first and second axes substantially concurrently.

7. The insertion guide device of claim 6, wherein the pulling member is a threaded member that is threadably received by the base contacting portion, the threaded member selectively threadably advancing relative to the base contacting portion to selectively pull the base portion, the first portion, and the second portion together to selectively fix the insertion axis relative to the first and second axes substantially concurrently.

8. The insertion guide device of claim 7, further comprising a gripping device that is coupled to the threaded member for threadably advancing the threaded member.

9. The insertion guide device of claim 6, wherein the base portion includes a base lip and the base contacting portion includes a contacting lip, the base lip and the contacting lip selectively abutting to selectively fix the insertion axis relative to the first and second axes substantially concurrently.

10. The insertion guide device of claim 9, wherein one of the base lip and the contacting lip extends radially inward toward the insertion axis and the other of the base lip and the contacting lip extends radially outward away from the insertion axis.

11. The insertion guide device of claim 10, wherein the base lip is annular.

12. The insertion guide device of claim 1, wherein the insertion guide portion defines a through hole that defines the insertion axis.

13. The insertion guide device of claim 12, further comprising a set screw for selectively fixing the instrument within the through hole.

14. The insertion guide device of claim 1, wherein the locking device includes a first locking device and a second locking device, each for selectively and independently fixing the insertion guide portion relative to the base portion and selectively fixing the insertion axis relative to the first and second axes substantially concurrently, wherein the first and second locking device are disposed on opposite sides of the insertion axis.

15. The insertion guide device of claim 1, wherein the locking device includes a pulling member and a base contacting portion, the base contacting portion selectively engaging the base portion, the second portion disposed between the first portion and the base contacting portion, the pulling member and the base contacting portion cooperating to selectively pull the base portion, the first portion, and the second portion together to selectively fix the insertion axis relative to the first and second axes substantially concurrently, wherein the base portion includes a base lip and the base contacting portion includes a contacting lip, the base lip and the contacting lip selectively abutting to selectively fix the insertion axis relative to the first and second axes substantially concurrently, and wherein the base contacting portion includes a first portion that is disposed on a first side of the base lip and a second portion that is disposed on a second side of the base lip, the first side and the second side being opposite each other, the first portion operatively coupled to the pulling member, and the second portion selectively fixing to the base portion.

16. An insertion guide device for guiding an instrument toward a target location in a subject, the insertion guide device comprising:

a base portion securable to the subject;

a first portion;

an insertion guide portion defining an insertion axis, the insertion guide fixed relative to the first portion, the insertion guide portion guiding the instrument along the insertion axis, the insertion guide portion moveably supported by the base portion for movement of the insertion axis about at least two axes;

a second portion, the first portion moveably supported by the second portion for movement of the insertion axis about one of the at least two axes, the second portion disposed between the first portion and the base portion, the second portion moveably supported by the base portion for movement of the insertion axis about another of the at least two axes; and a locking device that selectively fixes the insertion guide portion relative to the base portion to fix the insertion axis relative to the at least two axes substantially concurrently;

wherein the locking device includes a pulling member and a base contacting portion, the base contacting portion selectively engaging the base portion, the second portion disposed between the first portion and the base contacting portion, the pulling member and the base contacting portion cooperating to selectively pull the base portion, the first portion, and the second portion together to selectively fix the insertion axis relative to the at least two axes substantially concurrently;

wherein the base portion includes a base lip and the base contacting portion includes a contacting lip, the base lip and the contacting lip selectively abutting to selectively fix the insertion axis relative to the at least two axes substantially concurrently;

wherein the base contacting portion includes a first portion that is disposed on a first side of the base lip and a second portion that is disposed on a second side of the base lip, the first side and the second side being opposite each other, the first portion operatively coupled to the pulling member, and the second portion selectively fixing to the base portion.

17. An insertion guide device for guiding an instrument through a hole in a subject toward a target location in the subject, the hole including an axis, the insertion guide device comprising:
- a base portion securable to the subject, the base portion including an annular lip that extends radially inward;
- an insertion guide portion defining a through hole that defines an insertion axis, the instrument receiveable in the through hole to be guided along the insertion axis;
- a first portion fixed to the insertion guide portion, the first portion defining a slot that curves about a first axis of rotation that is positionable to be perpendicular to the axis of the hole in the subject;
- a second portion disposed between the first portion and the base portion, the second portion rotatably supported by the base portion for rotation about a second axis of rotation that is positionable to be parallel to the axis of the hole in the subject; and
- a locking device that includes a gripping device, a threaded member, and a base contacting portion, the base contacting portion including a top portion that threadably receives the threaded member and a bottom portion having a lip, the lip extending radially inward, the threaded member moveably received in the slot of the first portion to limit rotation of the first portion and the insertion guide portion about the first axis of rotation, wherein upon rotating the gripping device the threaded member selectively threadably advances relative to the base contacting portion such that the lip of the base contacting portion selectively abuts the annular lip of the base portion and such that the threaded member and the base contacting portion cooperate to pull the base portion, the first portion, and the second portion together to concurrently fix the insertion axis relative to the first and second axes of rotation.

18. The insertion guide device of claim 17, wherein the locking device includes a first locking device and a second locking device, each for selectively and independently fixing the insertion guide portion relative to the base portion and selectively fixing the insertion axis relative to the at least two axes substantially concurrently, wherein the first and second locking device are disposed on opposite sides of the insertion axis.

\* \* \* \* \*